United States Patent
Gamelin et al.

(10) Patent No.: US 9,901,747 B2
(45) Date of Patent: Feb. 27, 2018

(54) PHOTOTHERAPY LIGHT ENGINE

(71) Applicant: Clarify Medical Inc., San Diego, CA (US)

(72) Inventors: Andre S. Gamelin, Vista, CA (US); Martyn C. Gross, San Diego, CA (US); Jack Schmidt, San Marcos, TX (US); William Jack MacNeish, III, Newport Beach, CA (US)

(73) Assignee: CLARIFY MEDICAL INC., San Diego, CA (US)

( * ) Notice: Subject to any disclaimer, the term of this patent is extended or adjusted under 35 U.S.C. 154(b) by 0 days.

(21) Appl. No.: 15/351,119

(22) Filed: Nov. 14, 2016

(65) Prior Publication Data

US 2017/0056686 A1  Mar. 2, 2017

Related U.S. Application Data (63) Continuation of application No. PCT/US2016/024996, filed on Mar. 30, 2016.
(Continued)

(51) Int. Cl.
*A61N 5/06* (2006.01)
*H01L 25/075* (2006.01)
(Continued)

(52) U.S. Cl.
CPC ........ *A61N 5/0616* (2013.01); *H01L 25/0753* (2013.01); *H01L 33/483* (2013.01); *H01L 33/58* (2013.01); *H01L 33/60* (2013.01); *H01L 33/62* (2013.01); *H01L 33/641* (2013.01); *H01L 33/648* (2013.01); *H02J 7/0021* (2013.01); *H02J 7/0044* (2013.01); *A61B 34/25* (2016.02); *A61N 5/0618* (2013.01);
(Continued)

(58) Field of Classification Search
CPC ............................... A61N 5/0616; A61N 5/06
USPC ..................................................... 607/88, 90
See application file for complete search history.

(56) References Cited

U.S. PATENT DOCUMENTS 5,720,772 A   2/1998   Eckhouse
5,836,999 A   11/1998  Eckhouse et al.
(Continued)

FOREIGN PATENT DOCUMENTS

CA   2387071 A1   2/2002
CA   2452408 A1   1/2003
(Continued)

OTHER PUBLICATIONS

PCT Patent Application No. PCT/US2016/024996 International Search Report and Written Opinion dated Jul. 1, 2016.
(Continued)

*Primary Examiner* — William Thomson
*Assistant Examiner* — Victor Shapiro
(74) *Attorney, Agent, or Firm* — Wilson Sonsini Goodrich & Rosati (57) ABSTRACT

Described herein are devices, systems, and methods for delivering phototherapy to a subject. A phototherapy light engine is combined with other components to form a phototherapy system that provides phototherapy treatment to a subject. A phototherapy system may be implemented as a hand held system comprising the light engine that is configured to communicate with a remote computing device.

16 Claims, 7 Drawing Sheets

Related U.S. Application Data (60) Provisional application No. 62/146,124, filed on Apr. 10, 2015.

(51) Int. Cl.

| | | |
|---|---|---|
| *H01L 33/48* | (2010.01) | |
| *H01L 33/58* | (2010.01) | |
| *H01L 33/60* | (2010.01) | |
| *H01L 33/62* | (2010.01) | |
| *H02J 7/00* | (2006.01) | |
| H01L 33/64 | (2010.01) | |
| A61B 34/00 | (2016.01) | |
| A61N 5/00 | (2006.01) | |

(52) U.S. Cl.
CPC ..... *A61N 2005/005* (2013.01); *A61N 2005/0644* (2013.01); *A61N 2005/0652* (2013.01); *A61N 2005/0661* (2013.01); *A61N 2005/0666* (2013.01); *H01L 33/64* (2013.01)

(56) References Cited

U.S. PATENT DOCUMENTS

| | | | |
|---|---|---|---|
| 6,063,108 A | 5/2000 | Salansky et al. | |
| 6,290,713 B1 | 9/2001 | Russell | |
| 6,413,268 B1 | 7/2002 | Hartman | |
| 6,663,659 B2 | 12/2003 | McDaniel | |
| 6,835,202 B2 | 12/2004 | Harth et al. | |
| 6,902,563 B2 | 6/2005 | Wilkens et al. | |
| 7,081,128 B2 | 7/2006 | Hart et al. | |
| 7,087,074 B2 | 8/2006 | Hasegawa | |
| 7,252,628 B2 | 8/2007 | Van et al. | |
| 7,276,059 B2 | 10/2007 | Irwin | |
| H2242 H | 7/2010 | Gonzales | |
| 7,886,749 B2 | 2/2011 | Irwin | |
| 7,887,533 B2 | 2/2011 | Barolet et al. | |
| 7,921,853 B2 | 4/2011 | Fiset et al. | |
| 7,985,219 B2 | 7/2011 | Wilkens et al. | |
| 8,157,807 B2 | 4/2012 | Ferren et al. | |
| 8,435,273 B2 | 5/2013 | Lum et al. | |
| 8,486,056 B2 | 7/2013 | Irwin | |
| 8,486,124 B2 | 7/2013 | Hendrix et al. | |
| 8,518,027 B2 | 8/2013 | Weckwerth et al. | |
| 8,518,094 B2 | 8/2013 | Wang | |
| 8,523,849 B2 | 9/2013 | Liu et al. | |
| 8,620,451 B2 | 12/2013 | Kennedy | |
| 8,801,254 B2 | 8/2014 | McNeill et al. | |
| 8,864,362 B2 | 10/2014 | Sherman et al. | |
| 2002/0128695 A1 | 9/2002 | Harth et al. | |
| 2004/0054386 A1 | 3/2004 | Martin et al. | |
| 2004/0188696 A1 | 9/2004 | Hsing et al. | |
| 2005/0157515 A1 | 7/2005 | Chen et al. | |
| 2005/0196720 A1 | 9/2005 | Ostler et al. | |
| 2006/0085053 A1 | 4/2006 | Anderson et al. | |
| 2006/0289887 A1 | 12/2006 | Bui et al. | |
| 2009/0240310 A1 | 9/2009 | Kennedy | |
| 2010/0127299 A1 | 5/2010 | Smith et al. | |
| 2011/0037002 A1 | 2/2011 | Johnson et al. | |
| 2012/0022618 A1 | 1/2012 | Lum et al. | |
| 2012/0059441 A1 | 3/2012 | Chang et al. | |
| 2012/0078329 A1 | 3/2012 | Shimada | |
| 2012/0165907 A1 | 6/2012 | Wagenaar et al. | |
| 2013/0013032 A1 | 1/2013 | Irwin | |
| 2013/0030264 A1 | 1/2013 | Gopalakrishnan et al. | |
| 2013/0115180 A1 | 5/2013 | Goren et al. | |
| 2013/0144364 A1* | 6/2013 | Wagenaar Cacciola ........... A61N 5/0613 607/90 | |
| 2013/0172963 A1 | 7/2013 | Moffat | |
| 2013/0190841 A1 | 7/2013 | McMillan | |
| 2013/0245724 A1 | 9/2013 | Kaufman | |
| 2013/0282080 A1 | 10/2013 | Hendrix et al. | |
| 2013/0317574 A1 | 11/2013 | Gourgouliatos et al. | |
| 2013/0345687 A1 | 12/2013 | McMillan et al. | |
| 2014/0031906 A1 | 1/2014 | Brezinski | |
| 2014/0039473 A1 | 2/2014 | Liu et al. | |
| 2014/0277299 A1 | 9/2014 | Intintoli et al. | |
| 2014/0288351 A1 | 9/2014 | Jones | |
| 2014/0303547 A1 | 10/2014 | Loupis et al. | |
| 2015/0022093 A1 | 1/2015 | Smith et al. | |
| 2015/0025601 A1 | 1/2015 | Fiset | |
| 2015/0025602 A1 | 1/2015 | Wagenaar et al. | |
| 2015/0165229 A1 | 6/2015 | Rodrigues | |
| 2015/0217130 A1 | 8/2015 | Gross et al. | |

FOREIGN PATENT DOCUMENTS

| | | |
|---|---|---|
| CA | 2767594 A1 | 1/2011 |
| CA | 2861620 A1 | 7/2013 |
| CN | 1578688 A | 2/2005 |
| CN | 1728971 A | 2/2006 |
| CN | 1250302 C | 4/2006 |
| CN | 102006833 A | 4/2011 |
| CN | 102470252 A | 5/2012 |
| CN | 102481456 A | 5/2012 |
| CN | 102811766 A | 12/2012 |
| CN | 102870020 A | 1/2013 |
| CN | 104168953 A | 11/2014 |
| CN | 104640602 A | 5/2015 |
| EP | 1307261 A1 | 5/2003 |
| EP | 1575436 A1 | 9/2005 |
| EP | 2252229 A1 | 11/2010 |
| EP | 2258301 A2 | 12/2010 |
| EP | 2445586 A1 | 5/2012 |
| EP | 2448635 A2 | 5/2012 |
| EP | 2451528 A1 | 5/2012 |
| EP | 2494389 A2 | 9/2012 |
| EP | 2670334 A1 | 12/2013 |
| EP | 2800605 A1 | 11/2014 |
| EP | 2877243 A1 | 6/2015 |
| JP | 2012531938 A | 12/2012 |
| KR | 101349157 B1 | 1/2014 |
| WO | WO-2001014012 | 3/2001 |
| WO | WO-2003001984 | 1/2003 |
| WO | WO-2004054458 | 7/2004 |
| WO | WO-2008061197 A2 | 5/2008 |
| WO | WO-2009113986 | 9/2009 |
| WO | WO-2011001344 | 1/2011 |
| WO | WO-2011004170 | 1/2011 |
| WO | WO-2011053804 | 5/2011 |
| WO | WO-2011109628 | 9/2011 |
| WO | WO-2013020179 | 2/2013 |
| WO | WO-2013103743 A1 | 7/2013 |
| WO | WO-2013138517 A1 | 9/2013 |
| WO | WO-2014018103 | 1/2014 |
| WO | WO-2014076503 A1 | 5/2014 |
| WO | WO-2014131115 A1 | 9/2014 |
| WO | WO-2015041919 A1 | 3/2015 |
| WO | WO-2017019455 A2 | 2/2017 |

OTHER PUBLICATIONS

U.S. Appl. No. 14/613,297 Office Action dated Feb. 8, 2017.
European Patent Application No. 15743284.0 extended European Search Report dated Sep. 5, 2017.

* cited by examiner

PHOTOTHERAPY LIGHT ENGINE

CROSS-REFERENCE

This application is a Continuation of International Application No. PCT/US2016/024996 entitled "PHOTOTHERAPY LIGHT ENGINE" filed Mar. 30, 2016, which claims the benefit of U.S. Provisional Application Ser. No. 62/146,124, entitled "PHOTOTHERAPY LIGHT ENGINE" filed on Apr. 10, 2015, the content of which each application is herein incorporated herein by reference in its entirety.

BACKGROUND OF THE INVENTION

Phototherapy is exposure of a subject to either natural sunlight or light generated by an artificial light source in order to treat a lesion, disease, or condition of the subject. Certain wavelengths or a range of wavelengths of light have been found to provide optimal therapy for particular lesions, diseases or conditions. The UVB range is an example of a particularly therapeutic range of wavelengths.

Light emitting diodes are a light source that may be used to generate light in a wavelength range suitable for use with phototherapy. A light emitting diode comprises a two-lead semiconductor light source, which emits light when activated. When a suitable voltage is applied to the leads of a light emitting diode, energy is released in the form of photons. Modern light emitting diodes may be configured to release photons of various wavelengths including wavelengths in the ultraviolet range including wavelengths in the UVB range.

Phototherapy is currently used to treat a range of disorders and diseases including dermatologic diseases, sleeping disorders, and psychiatric disorders.

SUMMARY OF THE INVENTION

Described herein are devices, systems, and methods that deliver light for phototherapy to a subject. The devices, systems, and methods described herein are adapted for delivery of phototherapy in terms of their mode of delivery of phototherapy, uniformity of light administered to a treatment site, the power of the photo-output that is achievable, and the relatively low cost of production, among other things.

The mode of delivery described herein is adapted in that the devices, systems, and methods described herein may be implemented with a hand-held device. Traditional phototherapy providing devices are large and cumbersome, and are thus not suitable for hand held use. Hand held use is advantageous because, for example, it is a convenient mode in terms of ease of use for the subject, and hand held use is additionally advantageous because, for example, hand held use allows a subject to direct therapy directly to an area requiring treatment. Hand held usage is achievable, in part at least, due to the suitability of use of light emitting diodes in providing phototherapy. Light emitting diodes have a very small die size which is typically less than 1 square millimeter. Individually packaged light emitting diodes are also small having a size that is typically less than 15 square millimeters. Light emitting diodes also have the advantage that they can be driven with low voltage electronics that reduces the size of the power electronics and enables the device to be easily driven with a battery-powered supply. The small size of light emitting diodes allows the use of the light emitting diodes in arrays that are themselves relatively small in diameter or in size, and can be combined with other relatively small components to form a unique phototherapy device adapted for hand held use.

The power of the photo-output that is achievable is also adapted in the devices, systems, and methods described herein. An improved photo-output is advantageous because, for example, it may be expected to decrease treatment time, thus increasing treatment compliance, and is also advantageous because, for example, it may provide a more cost effective treatment. The improved power output is achieved, at least in part, due to the use of thermal control in combination with the use of multiple reflectors and reflector types. It is common for light emitting diode output to drop dramatically as the temperature of the light emitting diode increases. In some cases this output can drop below 50% of the achievable power just from self-heating. Furthermore, controlling the temperature rise may permit the devices described herein to drive light emitting diodes at higher power levels without suffering efficiency losses associated with higher operating temperatures. Additionally, utilizing reflectors may permit the devices described herein to direct the emitted light to the target area with improved efficiency. Light emitting diodes typically output light in all directions and in some cases more than 50% of the emitted light may be lost from absorption into surrounding materials without the use of reflectors.

The systems and devices described herein are also adapted in terms of cost of production. High cost is generally a barrier to entry in the phototherapeutics market. A lower cost of production is advantageous because, for example, it will allow the device to be provided for home use at an affordable cost. The reduction of cost is achievable, at least in part, because the efficiency gains from the use of thermal control and reflectors allows for a reduction in the number of LEDs for light emissions required for phototherapy.

Specifically, described herein is a phototherapy light engine device comprising a thermally conductive core substrate having a first and a second surface, a plurality of light emitting diodes configured to couple with said first surface of said thermally conductive metal core substrate, a plurality of light reflectors coupled to said first surface of said thermally conductive metal core substrate, a collar coupled to said first surface of said thermally conductive core substrate, a window coupled to said collar and positioned to cover at least part of said thermally conductive core substrate, and a heat sink coupled to said second surface of said thermally conductive metal core substrate.

Also described herein is phototherapy system comprising a light engine which comprises a thermally conductive core substrate and a plurality of light emitting diodes configured to couple to said thermally conductive core substrate, along with one or more current drivers configured to drive said plurality of light emitting diodes, a microprocessor coupled to said current driver, wherein said microprocessor controls said current output of said current driver, a user interface coupled to said microprocessor, wherein said user interface is configured to provide said user with control over said plurality of light emitting diodes, and a wireless receiver coupled to said microprocessor.

Also described herein is a method for thermally compensating a phototherapy device, said method comprising providing a phototherapy system to a subject comprising a thermally conductive core substrate coupled to a plurality of light emitting diodes along with a thermistor that is either thermally or physically coupled to said thermally conductive core substrate, a microprocessor that is either coupled with or comprises a retrievable data storage memory, and recording, with said thermistor, temperature data during operation of said phototherapy system. The method also comprises adjusting, with said microprocessor, based on said temperature data, at least one of a duration of light emission from said plurality of light emitting diodes and an amount of power supplied to said plurality of light emitting diodes and storing, using said retrievable data storage memory, said temperature data.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the devices, systems, and methods described herein are set forth with particularity in the appended claims. A better understanding of the features and advantages of devices, systems, and methods described herein will be obtained by reference to the following detailed description that sets forth illustrative embodiments, in which the principles of the invention are utilized, and the accompanying drawings of which:

DETAILED DESCRIPTION OF THE INVENTION

Described herein are devices, systems, and methods for providing phototherapy to a subject. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Described herein are devices, systems, and methods for providing phototherapy to a subject. In an embodiment, a phototherapy device comprises a light engine. A light engine comprises one or more light emitting diodes configured to deliver phototherapy to a subject.

In an embodiment a light engine comprises one or more light emitting diodes coupled to a thermally conductive core substrate. The thermally conductive core substrate may comprise metal or a non-metal material. In an embodiment, a thermally conductive core substrate comprises aluminum. Other non-limiting examples of metals suitable for use as a thermally conductive metal core substrate comprise copper, gold, iron, lead, nickel, silver, and titanium as well as alloys of these metals with each other and any other metal or metals. In an embodiment, a thermally conductive material comprises ceramic. In an embodiment the thermally conductive core substrate is approximately 1 mm in thickness. In an embodiment the thermally conductive core substrate thickness is in the range of 0.5 mm to 5 mm. In an embodiment the thermally conductive core substrate thickness is in the range of 0.5 mm to 10 mm. In an embodiment the thermal conductivity of the substrate is in the range of 1 W/mK to 5 W/mK.

In an embodiment, one or more light emitting diodes are coupled with a thermally conductive core substrate. A plurality of light emitting diodes may comprise, for example, at least one bare die light emitting diode. A plurality of light emitting diodes may entirely comprise, for example, non-bare die light emitting diodes. A plurality of light emitting diodes may entirely comprise, for example, bare die light emitting diodes. A bare die light emitting diode comprises a light emitting diode that is free from additional packaging typically used with light emitting diodes. An exemplary benefit of a bare die light emitting diode, in comparison to a non-bare die light emitting diode, is the absence of material that inhibits thermal conduction to the LED junction. Other exemplary benefits of a bare die light emitting diode, in comparison to a non-bare die light emitting diode, is improved energy efficiency and the absence of thermal limitation associated with typcial light emitting diode packaging. Another exemplary benefit of a bare die light emitting diode, in comparison to a non-bare die light emitting diode, is the absence of materials that reduce or constrain the optical output of the LED. In an embodiment, a plurality of light emitting diodes are arranged in an array on a surface of a thermally conductive core substrate. In an embodiment, a plurality of optically transmissive covers are positioned in direct contact with said light emitting diodes without an air gap, for reducing optical losses from internal refraction between said light emitting diodes and air. In an embodiment the transmissive covers are composed of silicone or a formulation based on silicone.

In an embodiment, one or more light emitting diodes is/are directly coupled to a thermally conductive core substrate. A light emitting diode may be directly coupled to a thermally conductive core substrate by, for example, soldering of the light emitting diode directly to the thermally conductive core substrate. In other embodiments the light emitting diodes are attached with a conductive epoxy or fused by using a sintering process.

In an embodiment, one or more light emitting diodes is/are coupled to contact pads which are in turn coupled to a thermally conductive core substrate. In an embodiment, the contact pads are separated from the thermally conductive core substrate by a thin dielectric layer for electrically insulating the contact pads from the thermally conductive core substrate.

In an embodiment, a contact pad has an area that is substantially wider and/or larger than the area of a light emitting diode. An exemplary benefit of large contact pad area is to provide a larger area for heat to transfer from the contact pad through the dielectric medium to the thermally conductive core substrate. In this embodiment, heat generated by the light emitting diode is dispersed through the surface of the contact pad rather than being transferred directly from the light emitting diode to the thermally conductive core substrate.

In an embodiment, a contact pad comprises a thermally conductive metal. Non-limiting examples of metals suitable for use as thermally conductive metal comprise copper, tin, gold, iron, lead, nickel, silver, and titanium as well as alloys of these metals with each other and any other metal or metals.

In an embodiment, the area of a contact pad is about 6 square millimeters, or approximately 50 times the contact area on the light emitting diode. In an embodiment, the area of a contact pad is about 10 square millimeters. In an embodiment, the area of a contact pad is about 9 square millimeters. In an embodiment, the area of a contact pad is about 8 square millimeters. In an embodiment, the area of a contact pad is about 7 square millimeters. In an embodiment, the area of a contact pad is about 5 square millimeters. In an embodiment, the area of a contact pad is about 4 square millimeters. In an embodiment, the area of a contact pad is about 3 square millimeters. In an embodiment, the area of a contact pad is about 2 square millimeters. In an embodiment, the area of a contact pad is about 1 square millimeter.

In an embodiment, a plurality of light emitting diodes are arranged in a plurality of strings. Each string of light emitting diodes may, for example, be driven separately, or, for example, the current in each string may be matched. In an embodiment, the drive current of each string is adjusted independently to improve the optical uniformity at the output of the light engine.

In an embodiment, one or more light emitting diodes is/are positioned so that they are recessed back relative to a phototherapy target area to be treated. Recessed light emitting diodes produce light that mixes together within the recessed space before being delivered to a, for example, targeted skin surface. In another embodiment, the light emitting diodes are arranged approximately equidistant to one another, to produce light of uniform intensity on the targeted surface. In another embodiment reflectors are positioned and angled in a manner to produce light of uniform intensity on the targeted surface.

In an embodiment, a light engine further comprises one or more reflectors. The one or more reflectors may comprise a reflective metal such as, for example, aluminum. The one or more reflectors may comprise a material coated with a reflective coating. The reflectors may, for example, comprise a polymer with an aluminum film deposited on the surface.

In an embodiment, one or more cone shaped reflectors have a one to one relationship with one or more light emitting diodes, wherein each light emitting diode on the surface of the thermally conductive substrate is positioned inside of a cone shaped reflector. Alternatively or additionally, a plurality of light emitting diodes may be positioned inside an area with reflectors at the perimeter.

In an embodiment, a plurality of cone shaped reflectors are connected to each other, forming a single unit having a shape and configuration similar to an egg carton.

In an embodiment, a light engine further comprises a housing, wherein the housing has at least one opening or aperture. In an embodiment, the thermally conductive core substrate is positioned within the housing and is recessed relative to the opening or aperture on the housing so that the light emitting diodes are recessed relative to the opening or aperture. The interior walls of the housing may be lined with reflectors. The interior walls of the housing may comprise reflectors. The interior walls of the housing may comprise a reflective coating. Reflectors on the interior surface of the housing may be positioned perpendicularly to the thermally conductive core substrate, or, alternatively reflectors may be positioned at an angle to the thermally conductive core substrate.

In an embodiment, a light engine further comprises a window positioned in the opening or aperture of the housing. In an embodiment, the window is positioned and sized so that it covers the entire array of light emitting diodes. The window may comprise, for example, acrylic. The window may comprise, for example, fused silica. In an embodiment, the window is UV transmissive.

In an embodiment, the window comprises a filter of light so that only light within a specific range is transmissive. For example, a window in this embodiment may be configured to be transmissive to light in the UVB wavelength. For example, a window in this embodiment may be configured to be transmissive to light having a wavelength in the range of 300-320 nanometers. In an embodiment, the window is attenuative to light outside of a desired wavelength. In this embodiment, attenuation may be achieved by, for example, coating the window with an absorptive optical coating. Alternatively, the attenuation may be achieved by a series of optical interference coatings. Alternatively or additionally, in this embodiment, the material of the window may be selected for filtering qualities that are innate to the material. Alternatively or additionally, in this embodiment, the thickness of the window may be selected for filtering qualities related to material thickness.

In an embodiment, a light engine further comprises a collar which defines a treatment area on, for example, a skin surface of a subject. A collar extends above the window so that the window is never in direct contact with the subject, but rather the collar is configured to be able to come into contact with the skin surface of a subject when contact with the skin surface of a subject is desired for effective treatment. In an embodiment, a collar extends directly from the walls of the housing, wherein the window is positioned within the housing so that the walls of the housing extend beyond the window. In an embodiment, the collar comprises the same material as the housing. In an embodiment, a collar comprises a soft, biocompatible material, for example, silicone. In an embodiment, a collar comprises a flexible material that conforms to body contours. In an embodiment, the collar defines the area over which the light emitted by the light emitting diodes is delivered. In an embodiment, the collar comprises a thin wall for reducing the importance of distinguishing between the treatment area defined by the inner wall and the perceived treatment area defined by the outer wall. In an embodiment, the collar is shaped as a square or rectangle in order to facilitate uniform treatment of an area that is larger than the treatment area defined by the collar, wherein a subject is able to move the device after each area is treated so that the rectangular or square shaped treated areas conveniently align with each other to cover the entire area to be treated. In an embodiment, a collar may be lined with reflectors. The collar may comprise reflectors. The collar may comprise a reflective coating. In an embodiment, reflectors on the interior surface of the collar are positioned at an angle that optimally delivers a uniform column of light, emitted by one or more light emitting diodes, through the window. In an embodiment, the collar comprises or is coupled to one or more sensors that indicate when the collar (and thus the device) is in contact with the skin. In this embodiment, a signal from the sensor, indicating contact with the skin, may cause the device to enable phototherapy, and a signal that indicates that the device is no longer in contact with the skin may cause the device to disable phototherapy. In an embodiment, the sensors are mechanical switches that are activated by depressing the collar.

In an embodiment, a light engine comprises a heat sink. In an embodiment, a heat sink is positioned on the surface of the thermally conductive core substrate that is opposite to the surface of the thermally conductive core substrate to which one or more light emitting diodes is/are coupled. The heat sink is configured to exchange heat to the environment through conduction. The heat sink, may, for example, comprise a thermally conducting material such as a thermally conductive metal such as, for example, aluminum. The heat sink may also, for example, comprise a thermally conductive plastic. In an embodiment, the heat sink is coupled to the enclosure. In another embodiment, the heat sink forms part of the enclosure. In an embodiment, a thermal compound is applied between the thermally conductive metal core substrate and the heat sink to aid in thermal coupling. In an embodiment, the heatsink is positioned within the thermally conductive core substrate and comprises a phase change assembly commonly known as a heat pipe.

In an embodiment, a heat sink is coupled to a fan which is positioned on the surface of the heat sink which is opposite to the surface facing the thermally conductive core substrate.

Also described herein is a phototherapy system which comprises a light engine coupled with one or more additional components. The one or more additional components may comprise a microprocessor, a computer readable storage medium comprising a retrievable memory, a current driver, a graphic user interface comprising or coupled with a display, a thermistor, a transmitter, and a receiver.

A current driver may comprise multiple channels such that the current driver is configured to individually drive separate strings of light emitting diodes. It may be desirable to separate light emitting diodes into strings to limit the voltage required to drive the string or to allow for an adjustment mechanism to improve uniformity of light emissions at the output of the system. In an embodiment, a current driver is configured to match the currents driven through each of the multiple channels. In an embodiment, a current driver is configured to detect short circuits or open circuits within a string of light emitting diodes. In an embodiment, the drive current of each string is separately adjustable to facilitate optimization of light emission uniformity.

A user interface may comprise a display. A user interface may alternatively or additionally comprise buttons, switches, or toggles. In an embodiment, a user may initiate a stored treatment or sequence of treatments using the user interface. A treatment may, for example, comprise a dose or duration of phototherapy intended for a treatment site. In an embodiment, the display shows a user the current treatment site and time remaining for the treatment.

A transmitter is configured to wirelessly transmit data to a computing device. Non-limiting examples of wirelessly transmitted signals may comprise, for example, an RF signal, an ultrasound, a Wi-Fi™ signal, or a Bluetooth™ signal. In an embodiment, the transmitter transmits a wireless signal comprising treatment data. Treatment data may comprise a regimen administered to a subject. Treatment data may alternatively or additionally comprise schedule data, which may comprise, for example, dates in which a subject previously received phototherapy via the light engine. A computing device that receives a wirelessly transmitted signal from the light engine may comprise a remote server. A computing device that receives a wirelessly transmitted signal from the light engine may comprise a mobile computing device such as, for example, a smartphone, tablet computer, or laptop computer.

A receiver is configured to receive wireless data from a computing device. Non-limiting examples of wirelessly received signals may comprise, for example, an RF signal, an ultrasound, a Wi-Fi signal, or a Bluetooth signal.

Wireless data received may comprise prescribed treatment sites and doses, configuration information and other program information. For example, a wirelessly received communication could enable the device user interface for a prescribed treatment sequence.

A thermistor may, for example, be coupled to the thermally conductive metal core material. A "thermistor", as the term is used herein, may refer to any temperature measurement device which could be a thermistor, resistance temperature device, thermocouple or temperature measurement integrated circuit. A thermistor measures temperature that represents, for example, the temperature of the thermally conductive metal core material or the light emitting diodes. The light emissions of the light emitting diodes are directly related to the power driven through the light emitting diodes and the temperature of the light emitting diodes. The temperature of the light emitting diodes may be measured by the thermistor and communicated to the microprocessor.

In an embodiment, a phototherapy system may further comprise an optical power measurement device positioned between a plurality of light emitting diodes and an optical window for measuring and calibrating light emissions.

The microprocessor may be coupled to other components including but not limited to the current driver, the display, the user interface, a thermistor, and a wireless transmitter and a receiver. The microprocessor may be coupled to other components in such a way that allows both one and two way communication between the microprocessor and the other components. A communication from a microprocessor to a current driver may, for example, pass current through a channel. A communication from a current driver to a microprocessor may, for example, may identify a detected short circuit or open circuit. In an embodiment, a signal communicated from the microprocessor to the current driver may turn the current driver on or off. In an embodiment, a microprocessor may cause the display to guide the user through a sequence of treatments. A user interface may provide a subject controls to initiate treatment commands to the microprocessor. In an embodiment, a microprocessor receives temperature data from a thermistor.

In an embodiment, the system output is calibrated by measuring the optical output and temperature of the system over the range of operation of the system and storing this calibration information in the device memory. In another embodiment, the system output is calibrated by measuring the optical output and temperature of the system at one or more operating temperatures and using known performance information to fill in the output table. In another embodiment, the temperature measured by the thermistor is used by the microprocessor to adjust the treatment time in accordance with known or measured output characteristics of the light engine. For example, if the system is calibrated to output 100 mW at a thermistor temperature of 40 C, and 90 mW at a thermistor temperature of 45 C, then a 60 second treatment intended for 100 mW of power at 40 C would run for 66 seconds on a warmer day where the thermistor temperature read 45 C.

In an embodiment, a microprocessor causes data to be transmitted through the wireless transmitter, which may, for example, comprise subject or treatment data. In an embodiment, information that is received by the receiver is communicated to the microprocessor, wherein the received signal may comprise, for example, a program of therapy conditions to be administered. The microprocessor may be configured to code or decode transmitted and received signals. For example, subject information or treatment data may be coded or decoded by a microprocessor in order to, for example, protect patient private data. In an embodiment, a received command comprises a signal that is processed by the microprocessor. A command may comprise, for example, a signal to shut off current flow to one or more light emitting diodes or one or more light emitting diode strings. A microprocessor may comprise or be coupled to a computer readable storage medium comprising a memory. A computer readable storage medium may store, for example, subject identification data, therapy data, or performance data.

In an embodiment, data received by a receiver comprises data that was generated by another phototherapy device or a population of phototherapy devices. For example, optical performance data from a population of phototherapy devices may be received, communicated to the microprocessor, and then used by the microprocessor to make adjustments such as, for example, adjustments to compensate for LED output degradation over time under certain use conditions.

In an embodiment, a phototherapy system is powered by one or more batteries. In an embodiment, the battery voltage is boosted to supply power to a string of light emitting diodes. In an embodiment, battery powered light engine comprises a hand held device. The one or more batteries used in the light engine may be rechargeable batteries.

In an embodiment, a phototherapy system couples with a charging port or docking station configured to recharge the one or more rechargeable batteries when the charging port and light engine are coupled. In an embodiment, a docking station further comprises optical power measurement device for measuring and calibrating light emissions.

Figure 1A:
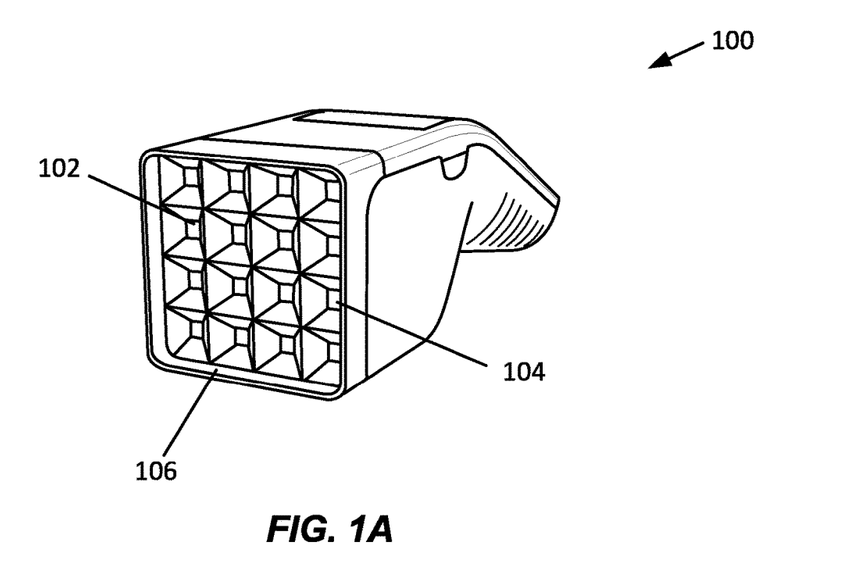
FIG. 1A shows an oblique frontal view of an embodiment of a phototherapy system described herein.
Figure 1B:
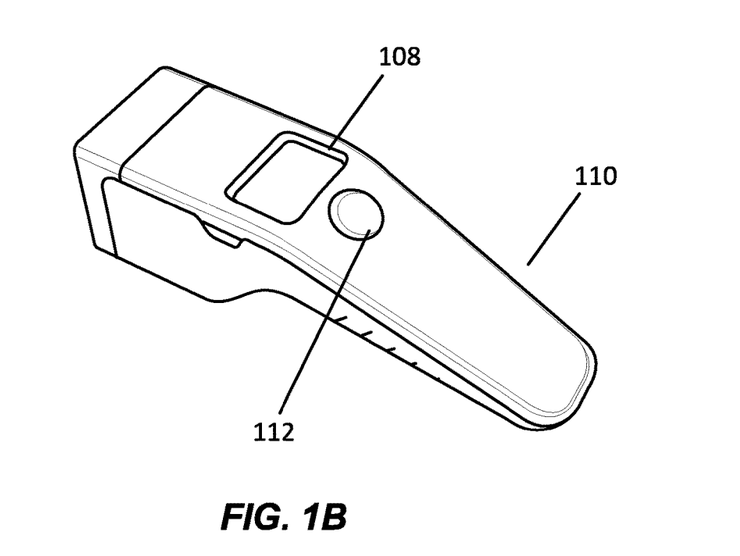
FIG. 1B shows an oblique top view of an embodiment of a phototherapy system described herein.

FIGS. 1A and 1B show a graphic representation of an embodiment of a light engine 100 according to an embodiment described herein. The device shown in FIGS. 1A and 1B comprises a hand held device 100. FIG. 1A is an oblique frontal view of the device 100. FIG. 1A shows a window 102. The window 102 is positioned within an opening in the housing of the device 100. The window 102 is positioned so that it covers the light producing area of a thermally conductive core substrate coupled with one or more light emitting diodes (not shown). The window 102 may be configured to filter or attenuate light wavelengths that are not therapeutic. Similarly, the window 102 may be configured to be highly transmissive of light at a desired wavelength such as, for example, light within the range of wavelengths of 300-320 nanometers. A cone shaped reflector 104 may be part of a single unit of other cone shaped reflectors. In the embodiment shown in FIG. 1A, there are sixteen total cone shaped reflectors, including cone shaped reflector 104, that are connected in a fashion similar to an egg carton. At least one light emitting diode (not shown) is positioned within each one of the cone shaped reflectors. A collar 106 that is fitted around the entire opening of the housing of the device 100 extends beyond the window 102. The collar 106 may comprise a compressible material that is configured to conform to fit curved body surfaces and also suitable to comfortably come into contact with the skin surface of a subject when contact with the skin surface of a subject is desired for effective treatment. When used to, for example, treat an area of a subject's skin, the device 100 is configured to be held against an area of skin of the subject in such a way that the outer edges of the collar 106 directly contact the subject's skin. That is to say, the subject (or someone else) holds the device 100 against the subject's skin so that the collar 106 contacts the skin of the subject in a way that positions window 100 directly over the target area (i.e. the treatment area). Once held over the area of the skin to be treated, light emitted by the light emitting diodes (not shown) passes through the window 102 to reach the skin area to be treated. The collar 106 may comprise reflectors on its interior surface or a reflective coating. When the device 100 is held in contact with the skin surface of a subject the collar 106 defines the surface area of treatment, wherein the area that is treated essentially comprises the same area defined by the borders of the collar 106. FIG. 1B shows a top view of device 100. Display screen 108 may comprise a digital display that may be coupled to a user control to form a graphical user interface. User control 112 is shown in FIG. 1B as a start switch. However, as described herein numerous other embodiments of user control 112 are suitable for use along with the systems, devices, and methods described herein. The handle 110, as shown in FIG. 1B, provides a subject or another with a convenient way to hold the device 100 while positioning the device 100 in contact with a skin surface of the subject.

Figure 2:
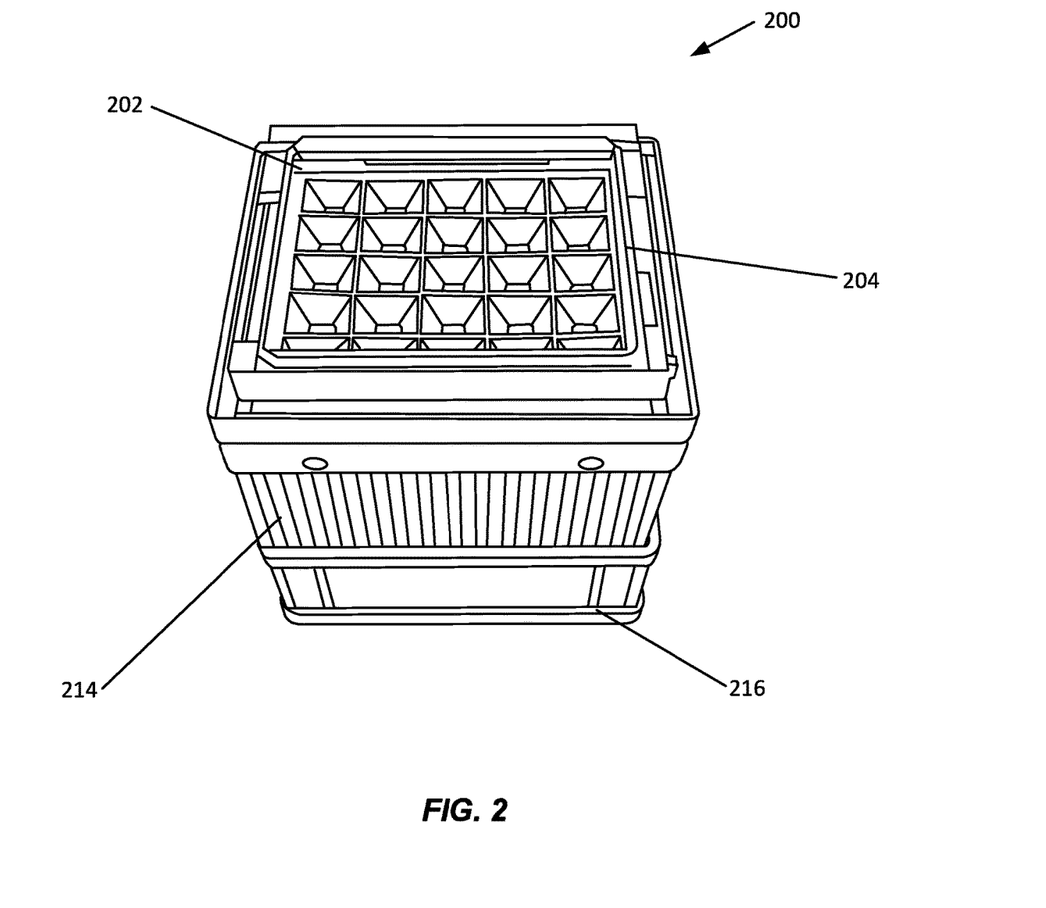
FIG. 2 shows an oblique top view of an embodiment of a light engine described herein.

FIG. 2 shows an embodiment of an oblique overhead view of a light engine device 200 according to an embodiment described herein. Window 202 is positioned over the light emitting diodes (not shown), the thermally conductive substrate material (not shown), and reflector cones (including the reflector cone 204). In this embodiment, reflector cone 204 is part of a larger unit that includes other interconnected reflector cones. A heat sink 214 is positioned underneath the thermally conductive substrate material (not shown), and reflector cones (including the reflector cone 204). The heat sink 214 passively conducts heat away from the light emitting diodes and thermally conductive substrate material when the device is operated. In this embodiment, the heat sink 214 is coupled to a fan 216 (fan housing is shown) which is positioned directly below the heat sink 214. The fan 216 functions to actively cool the device including the light emitting diodes and thermally conductive substrate material. The fan 216 may be powered by a battery or other power source (not shown) that powers the device 200.

Figure 3:
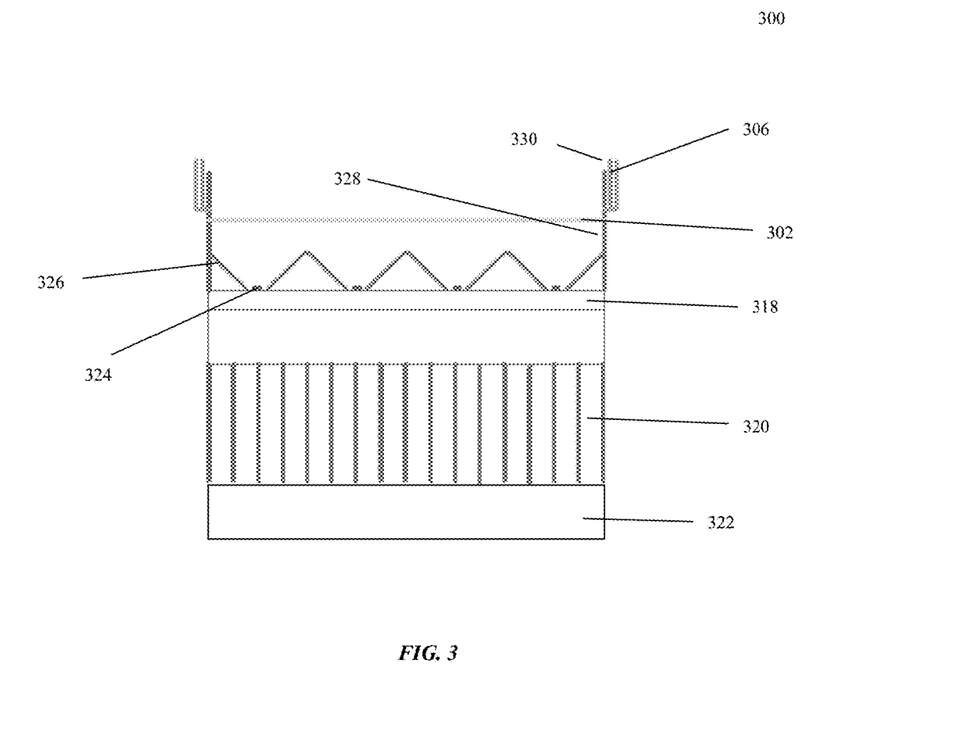
FIG. 3 shows a schematic of a frontal cross section of an embodiment of a light engine.

FIG. 3 shows a schematic of a frontal cross section of an embodiment of a light engine device 300 according to an embodiment described herein. Collar 306 extends beyond window 302. The collar 306 may comprise or be coupled with reflector 328. The reflector 328 extends continuously from the interior wall of the housing of the device 300 to beyond the window 302 along with the collar 306. The collar 306 may also comprise or be coupled with contact sensor 330 that transmits a signal when the collar 306 contacts a skin surface of a subject. A thermally conductive core substrate 318 is positioned below an array of light emitting diodes (including light emitting diode 324) and the cone reflectors (including cone reflector 326). A heat sink 320, as described herein, is positioned below the thermally conductive core substrate 318. A fan 322, as described herein, is positioned below the heat sink 320.

Figure 4:
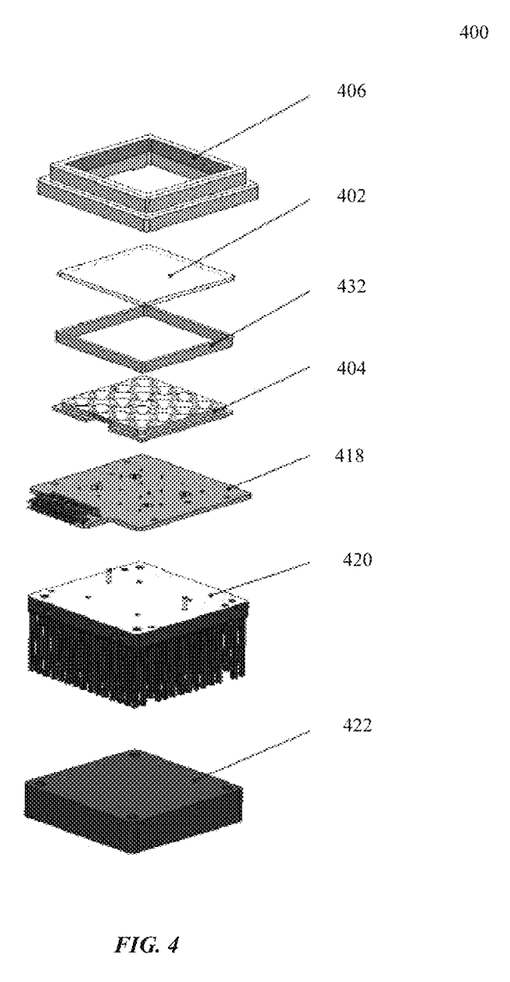
FIG. 4 shows an exploded view of an embodiment of a light engine described herein.

FIG. 4 shows an exploded view of an embodiment of a light engine device 400 according to an embodiment described herein. A collar 406 is shown with a frame fitting around window 402. A window spacer 432 with a reflective interior surface separates a window 402 from reflector cones 404. The window spacer 432 provides a space between an array of light emitting diodes and the window 402, such that the light emitting diodes are recessed relative to a targeted treatment site. Light emitted from recessed light emitting diodes is focused within the space provided by the window spacer 432 by the reflectors on the interior surface of the window spacer 432 as well as the cone shaped reflectors 404. Providing a space in which to focus the light from the one or more light emitting diodes in an array of light emitting diodes provides that the light that is delivered by the device is homogenous at the level of the targeted treatment site. A portion of the device housing may comprise window spacer 432 as described herein. A thermally conductive core substrate 418 as described herein is positioned between the cone shaped reflectors 404 and the heat sink 420. Heat sink 420 and fan 422 are shown positioned respectively beneath the thermally conductive core substrate 418 as described herein.

Figure 5:
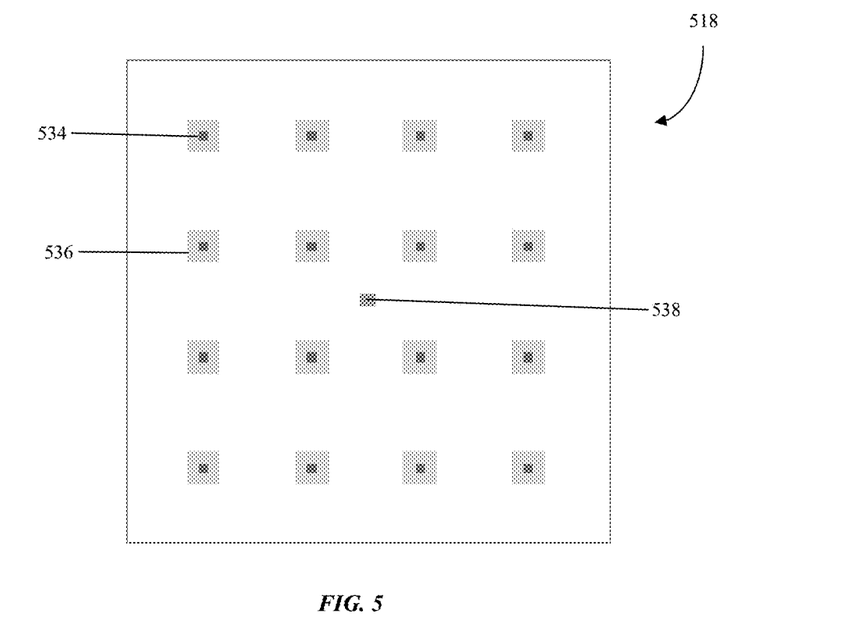
FIG. 5 is a schematic top view of a thermally conductive core substrate described herein.

FIG. 5 is a schematic top view of a thermally conductive core substrate 518 according to an embodiment described herein. One or more light emitting diodes 534 are positioned on a contact pad 536 as described herein. The light emitting diodes on the surface of the thermally conductive core substrate 518 may form an array. There may be one light emitting diode 534 per contact pad 536, or alternatively a light emitting diode 534 may be positioned on multiple contact pads 536. A thermistor 538, as described herein, is shown positioned on the thermally conductive core substrate 518. The thermistor 538 may be positioned in the center of the thermally conductive core substrate 518 as shown or at another position relative to the thermally conductive core substrate 518.

Figure 6:
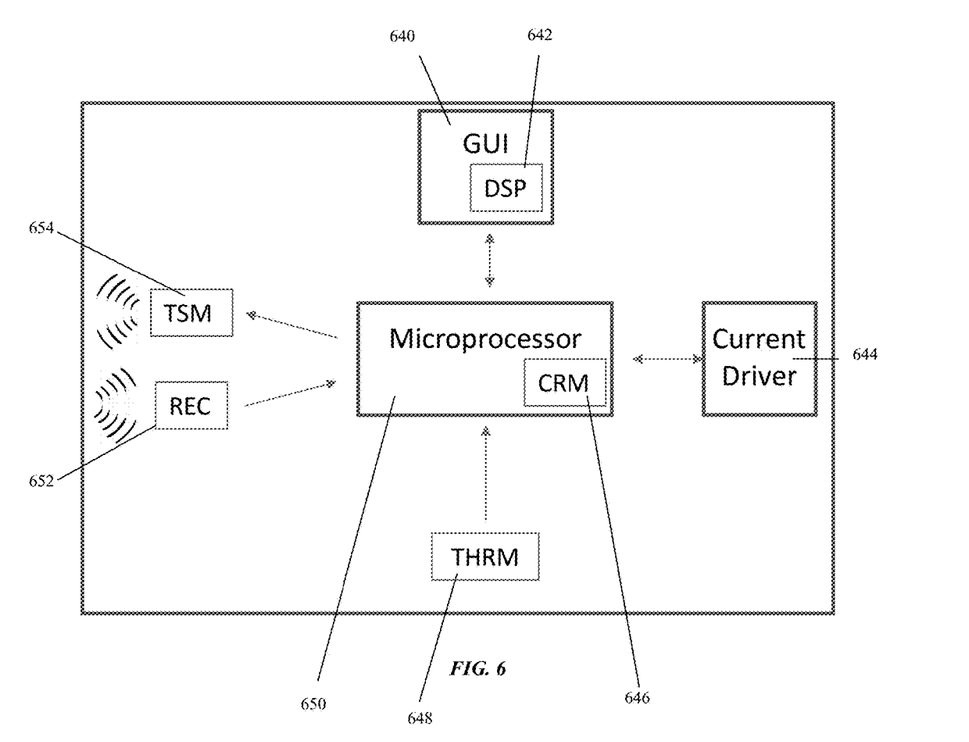
FIG. 6 is a schematic representation of components that combine with the light engine device to form a phototherapy system described herein.

FIG. 6 is a schematic representation of components that combine with the light engine device described herein to form a phototherapy system. A microprocessor 650, as described herein, may comprise or be coupled with a computer readable medium 646 comprising a memory. A computer readable medium 646 is configured to store software and data. Software stored on the computer readable medium 646 may be executed by the microprocessor 650, and may define how the microprocessor affects other components, such as, for example, a graphic user interface 640, or, for example, a current driver 644. Data stored on the computer readable medium 646 may comprise subject identifying information or treatment information. A graphic user interface 640 may further comprise or be coupled with a display 642. The microprocessor 650 may be configured to control the output on the display 642. Data and commands inputted by a subject into the graphic user interface 640 are transmitted to the microprocessor 650. Similarly, as described herein, the microprocessor 650 both controls and receives data from the current driver 644. The thermistor 648, as described herein, transmits temperature data to the microprocessor 650. Also, as described herein, receiver 652 transmits data and commands to the microprocessor 650, and, as described herein, microprocessor 650 transmits data to transmitter 654.

Figure 7:
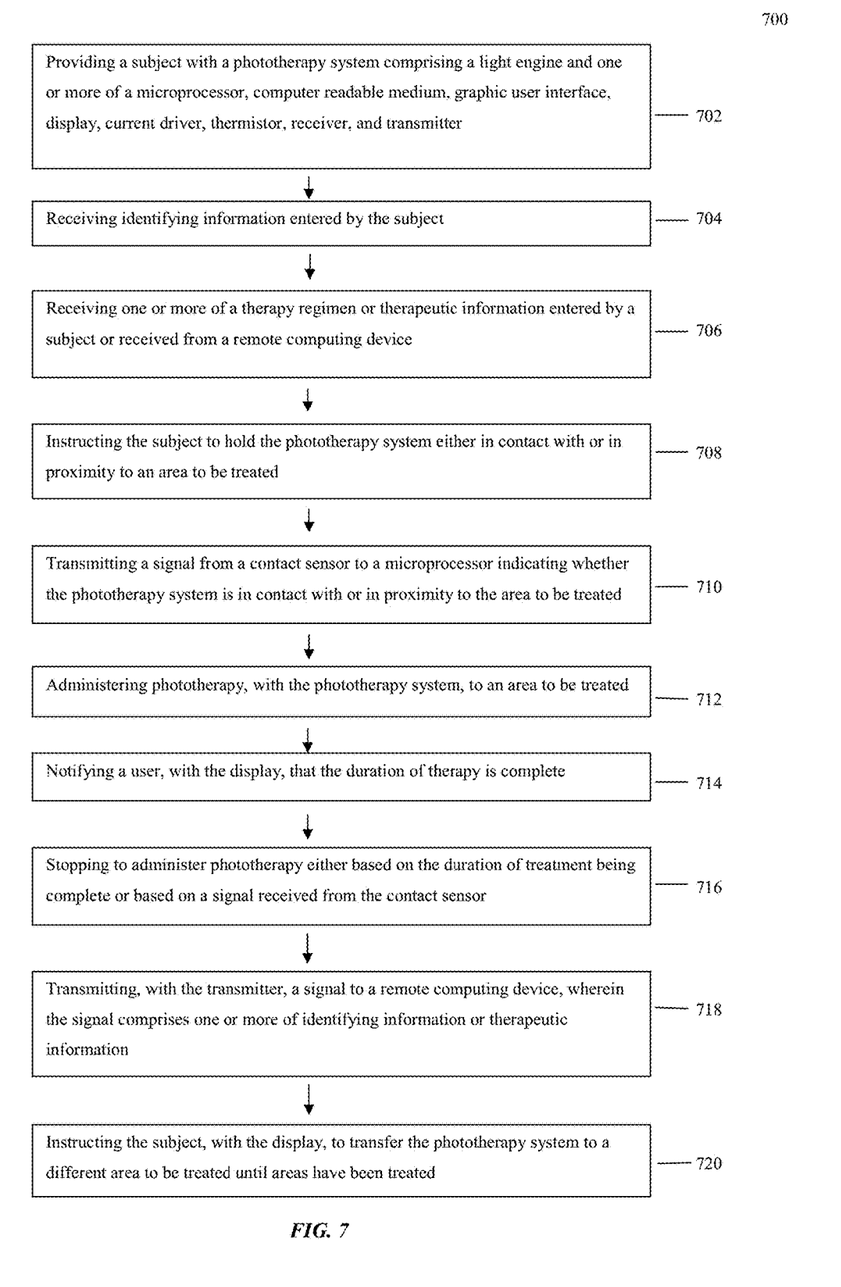
FIG. 7 is a schematic representation of a method for using devices and systems according to embodiments described herein.

FIG. 7 is a schematic representation of a method 700 for using the devices and systems described herein.

In step 702, a subject is provided with a phototherapy system described herein comprising a light engine described herein along with the additional components comprising the microprocessor, computer readable medium comprising a memory, the graphic user interface and display, the current driver, the thermistor, the receiver, and the transmitter.

In step 704, identifying information entered by a subject is received. Identifying information may comprise, for example, the subject's name, password or personal identification number. A subject may enter identifying information into the graphic user interface, which is in turn transmitted to the microprocessor and computer readable medium for storage.

In step 706, one or more of a therapy regimen or other therapeutic information is received. A therapy regimen may comprise, for example, a duration of a phototherapy treatment, an intensity of light to be delivered, or a site to be treated. Therapeutic information may comprise, for example, a treatment history, a schedule of treatment, or other non-phototherapy treatment instructions. A subject may enter or select a therapy regimen or therapeutic information through the graphic user interface. A subject may select and activate a therapy regimen using the graphic user interface, wherein the therapy regimen, for example, comprises phototherapy duration or intensity, which is in turn transmitted to the microprocessor and computer readable medium for storage. Alternatively or additionally, a therapy regimen or therapeutic information may be received from a remote computing device such as, for example, a therapy regimen or therapeutic information transmitted the receiver by a remote health care provider.

In a step 708, a subject is instructed to hold the phototherapy system described herein in contact with a targeted treatment area.

In step 710, a contact sensor transmits a signal to the microprocessor when the contact sensor contacts a skin surface of a subject. A signal received from the contact sensor indicating that the phototherapy system described herein is in contact with the skin surface of a subject causes the microprocessor to enable the light engine for phototherapy.

In step 712, phototherapy is administered by, for example, the subject pressing a start switch and maintaining the phototherapy system in contact with the treatment area until, for example, the display indicates that the treatment is over. Alternatively or additionally, another person may hold the device for the subject, or a mechanical device can be used to hold the phototherapy system in a fixed position such as, for example, a stand or clamp.

In step 714, the subject is notified that the treatment duration is complete. The subject may be notified in a number of ways such as, for example, an audible sound or a displayed message on a display screen.

In a step 716, the treatment is stopped by the microprocessor once the prescribed treatment time has elapsed. The phototherapy device will also stop providing therapy if a signal indicating that the device is no longer in contact with the treatment area is received from the contact sensor.

In step 718, one or more of identifying information or therapeutic information is transmitted from the phototherapy system via the transmitter to a computing device. Therapeutic information may comprise, for example, the duration of treatment, the location treated, or other treatment related data. The computing device may comprise a remote computing device such, as for example, a remote server. Alternatively or additionally, the computer may comprise a computing device of the subject such as a laptop, tablet, or smartphone.

In a step 720, a subject transfers the device to another area to be treated until all treatment areas are treated.

While preferred embodiments of the systems, devices, and methods described herein have been shown and described herein, it will be obvious to those skilled in the art that such embodiments are provided by way of example only. Numerous variations, changes, and substitutions will now occur to those skilled in the art without departing from the subject matter described herein. It should be understood that various alternatives to the embodiments of the systems, devices, and methods described herein may be employed in practicing the systems, devices, and methods described herein. It is intended that the following claims define the scope of the invention and that methods and structures within the scope of these claims and their equivalents be covered thereby.

What is claimed is:

1. A phototherapy light engine comprising:
   a. a thermally conductive core substrate having a first and a second surface;
   b. a plurality of light emitting diodes (LEDs) for emitting light comprising phototherapeutic component wavelengths, the plurality of LEDs configured to couple with said first surface of said thermally conductive core substrate, said thermally conductive core substrate for absorbing heat from said plurality of LEDs;
   c. a plurality of light reflectors functionally coupled to said plurality of LEDs for reflecting said emitted light, thereby directing said light toward a skin surface for treatment of a phototherapy subject;
   d. a window positioned to cover at least part of said first surface of said thermally conductive core substrate;
   e. a collar coupled to said first surface of said thermally conductive core substrate, said collar adapted to engage the skin surface and to limit escape of the emitted light from the skin surface and a surrounding area, wherein said collar is coupled to one or more sensors that cause the device to enable phototherapy when the collar is in contact with the skin surface of the phototherapy subject; and
   f. a heat sink coupled to said second surface of said thermally conductive core substrate, wherein said heat sink is configured and adapted to conduct heat away from said thermally conductive core substrate;
   wherein one or more of said plurality of light reflectors is positioned on the interior surface of the collar at the perimeter of the plurality of LEDs, and surrounds the plurality of LEDs.

2. The phototherapy light engine of claim 1, wherein said thermally conductive core substrate comprises aluminum.

3. The phototherapy light engine of claim 1, wherein said heat sink is functionally coupled to a fan.

4. The phototherapy light engine of claim 1, wherein said heat sink is functionally coupled to a thermally conductive enclosure.

5. The phototherapy light engine of claim 1, further comprising a plurality of contact pads coupled to at least one of said plurality of LEDs and to said first surface of said thermally conductive metal core substrate, for conducting heat from said plurality of said LEDs to said thermally conductive core substrate, said plurality of contact pads having an area that is larger than an area of at least one of the LEDs.

6. The phototherapy light engine of claim 1, wherein said plurality of LEDs comprises one or more bare die LEDs.

7. The phototherapy light engine of claim 6, further comprising a plurality of optically transmissive covers in direct contact with said bare die LEDs without an air gap therebetween, for reducing optical losses from internal refraction between said bare die LEDs and air.

8. The phototherapy light engine of claim 1, wherein said plurality of LEDs emit light in a therapeutic range comprising a UVB frequency range.

9. The phototherapy light engine of claim 8, wherein said UVB frequency range is about 300-320 nanometers.

10. The phototherapy light engine of claim 1, wherein one of said plurality of reflectors is cone shaped and is positioned and configured to reflect light emitted from exactly one of said plurality of LEDs.

11. The phototherapy light engine of claim 1, wherein said plurality of light reflectors comprise an aluminum reflector surface for reflecting the emitted light toward the skin surface.

12. The phototherapy light engine of claim 1, further comprising a housing configured for housing at least one of said thermally conductive core substrate, said heat sink, said plurality of LEDs, said plurality of light reflectors, said window and said collar.

13. The phototherapy light engine of claim 12, wherein said window is positioned within said housing so that a portion of a sidewall of said housing extends beyond said position of said window.

14. The phototherapy light engine of claim 1, wherein said window is adapted to filter some of the emitted light to block and/or attenuate light in certain wavelengths.

15. The phototherapy light engine of claim 13, wherein said portion of said sidewall of said housing that extends beyond said position of said window is coupled to a reflective surface for reflecting light inward and toward the skin surface.

16. The phototherapy light engine of claim 1, wherein said collar comprises a soft bio-compatible material.

* * * * *